US00PP09088P

United States Patent [19]

van Rosmalen

[11] Patent Number: Plant 9,088

[45] Date of Patent: Mar. 21, 1995

[54] *ANTHURIUM ANDREANUM* VARIETY NAMED CHAMPION

[75] Inventor: N. A. M. van Rosmalen, The Hague, Netherlands

[73] Assignee: Nic Van Der Knaap Anthuriumselecties B.V., Bleiswijk, Netherlands

[21] Appl. No.: 229,212

[22] Filed: Apr. 18, 1994

[51] Int. Cl.[6] ..... A01H 5/00

[52] U.S. Cl. ..... Plt./88.1

[58] Field of Search ..... Plt. 88.1

[56] References Cited

U.S. PATENT DOCUMENT

PP8713 5/1994 Lamb, et al. ..... PLT/88.1

*Primary Examiner*—Howard J. Locker

*Attorney, Agent, or Firm*—Foley & Lardner

[57] ABSTRACT

An Anthurium plant named Champion having leaf blades that are very small in comparison to the flowers, a flower with a distinctive shape having cupped spathe with an attractive red spadix, flowers which are held above the leaf canopy, a plant habit that is compact and full mainly due to vigorous shoot formation and leaves that are dark green, coriaceous and durable with decorative light green primary veins.

4 Drawing Sheets

The present invention comprises a new and distinct cultivar of Anthurium, botanically known as *Anthurium andreanum*, and referred to by the cultivar name Champion.

The new cultivar is a product of a planned breeding program carried out by the inventor N. A. M. van Rosmalen in Bleiswijk, The Netherlands, in 1989. The female or seed parent was an unnamed pink Anthurium cutflower designated 82-00-16 that was selected in 1982. The male or pollen parent was an unnamed white flowering potplant with small leaves designated 88-05-16 that was selected in 1988. Champion was discovered and selected as one flowering plant within the progeny of the stated cross by N. A. M. van Rosmalen in June 1990 in a controlled environment in a greenhouse in Bleiswijk. Subsequent asexual reproduction by tissue culture as performed at Bleiswijk, The Netherlands, has demonstrated that the combination of characteristics as herein disclosed for the new cultivar are firmly fixed and are retained through successive generations of asexual reproduction.

The following observations, measurements and values describe plants grown in Bleiswijk, The Netherlands, under greenhouse conditions which closely approximate those generally used in horticultural practice. Color references are made to The Royal Horticultural Society (RHS) Color Chart, except where general color terms of ordinary significance are used. The color values were determined between 11.30 AM and 3.00 PM on Jan. 4, 1994 under 10.000 lux natural light in a greenhouse in Bleiswijk.

Champion has not been observed under all possible environmental conditions. The phenotype may vary with variations in environment such as temperature, light intensity and day length, without any change in genotype.

The following traits have been repeatedly observed and are determined to be basic characteristics of Champion which in combination, distinguish this Anthurium as a new and distinct cultivar:

1. The lead blades are very small in comparison to the flowers.

2. The flower has a distinctive shape having a cupped spathe with an attractive red spadix.

3. The flowers are held well above the leaf canopy.

4. The plant habit is compact and full mainly due to vigorous shoot formation.

5. The leaves are dark green, coriaceous and durable with decorative light green primary veins.

The accompanying color photographic drawings show typical flower and foliage characteristics of Champion, with colors being as true as possible with illustrations of this type.

Sheet 1 is a photograph of the whole plant that shows the small size of the leaves compared to the flowers.

Sheet 2 is a closeup view of the cupped spathe with a top that bends downward.

Sheet 3 shows the old (green-red) and young (white) Champion flower.

Sheet 4 shows the dark green upper surface and light green lower surface of the Champion leaf blades.

Origin: Seedling produced by the cross of an unnamed selection designated 82-00-16 (female) and an unnamed selection designated 88-05-16 (male). The selection designated 82-00-16 is a pink cutflower and 88-05-16 is a white flowering potplant with small leaves.

Classification:

*Botanical.*—*Anthurium andreanum* L., cv. Champion.

*Commercial.*—Champion.

Propagation: Asexual production by tissue culture.

Plant: A Champion plant grown from tissue culture in a 14 cm pot for 65–70 weeks under appropriate growing conditions, will measure at maturity approximately 40 cm to 60 cm in height and approximately 30 cm to 40 cm in width.

Leaves

*Form.*—The leaf blade is ovate-cordate with an acuminate tip and a cordate base. The leaf blade angle with the petiole lays approximately between 90 and 140 degrees.

*Size.*—Champion produces abundant axillary shoots with small leaf blades resulting in wide variation in leaf blade length and width. The minimum leaf blade length is approximately 2 cm and the maximum leaf blade length is approximately 15 cm. The minimum leaf blade width is approximately 1.5 cm and the maximum leaf blade width is approximately 10 cm.

*Texture.*—The leaf blades are, in relation to the flowers, very small. The leaf blades are leathery and thick. The tip and lobes of mature leaf blades bend upwards to produce mature leaf blades that are cupped.

*Veins.*—The midvein and the other primary veins that radiate from the juncture of the petiole with the leaf protrude from the underside of the leaf blade. The light green color (upper surface: RHS 146C, lower surface: RHS 146D) of the midvein and primary veins (approximately 6 to 8) contrast with the dark green color of the upper surface of the leaf blade.

*Color.*—The upper surface of the leaf blade is dark green (RHS 139A) while the lower surface of the leaf blade lower surface is light green (RHS 146B).

*Lobes.*—A leaf blade has two lobes extending past the petiole. The distance from the juncture of the petiole and the leaf to the highest point on the lobes of the mature leaf blades (12 cm to 15 cm long) is approximately 4 cm to 5 cm.

*Petiole.*—The color of the petiole is green (RHS 144A) or red (RHS 39B to 39C) depending on the light intensity. The petiole has a thickening at the side where it is connected with the leaf blade. The length about which the petiole is thickened is approximately 2 cm to 3 cm. The cross-section of the petiole is round and the diameter is approximately 1 mm to 4 mm. The cataphyls of the petioles are approximately 8 cm to 10 cm long and the color is RHS 47B to 47C.

Inflorescence:

*Size.*—The flattened spathe is approximately 8 cm to 9 cm long and approximately 9 cm to 11 cm wide.

*Color.*—Upon opening fully the upper surface of the spathe is RHS 155C and the lower surface is RHS 155A. Depending on the time of the year, overblown flowers will die or fade. Faded flowers are still decorative. The spathe of a faded flower is green with red primary veins and a light brown tip. The color of the spathe fades as it ages such that the upper surface is RHS 144A and the lower surface is 144B. The veins are red only on the upper surface of the spathe (RHS 52B). The color of the tip is a mixture of small green and red sections.

*Arrangement.*—The spathe stands perpendicular on a straight wiry pedicel approximately 8 cm to 15 cm above the canopy. The pedicel is round in cross-section and has a diameter of approximately 4 mm to 5 mm. The pedicel has a straight seam in the longitudinal direction (from stem to spathe) on the side which is not covered by the spathe. The seam is not always clearly visible.

*Shape.*—The spathe is cordate with a cuspidate apex that is bent outwards and a cordate base. The spathe is cupped with the juncture of the spadix as the bottom. The spathe measures approximately 7 cm to 9 cm in height and approximately 9 cm to 11 cm in width. For completely developed flowers the depth of the spathe is, at the place where the spadix is connected with the spathe, approximately 3 cm to 4 cm. The spathe flattens as it ages but is never completely flat.

*Flowering time.*—After approximately 15 to 16 months for an untreated plant depending on season, approximately 6 to 9 blossoms will be present. Smaller blossoms may occur on less mature growth.

Reproductive organs:

*Size.*—The spadix is approximately 6 cm to 8 cm in height, a little bit shorter than the length of the spathe. The spadix is columnar in shape. The width at the top of an overblown spadix is approximately 6 mm to 8 mm and at the base approximately 9 mm to 11 mm. The angle of the spadix with the spathe is approximately 65 to 75 degrees.

*Color.*—The spadix has a red-orange top (RHS 34A) and a red base (RHS 47B) as the spathe unrolls. The spadix has a red top (RHS 47A) and red-purple base (RHS 53D) at the time of pollen expulsion.

*Stamens.*—Anthers and filaments are not clearly visible.

*Pollen.*—White in color.

*Pistil.*—Lighter than RHS 47A at the top and lighter than RHS 53D at the base. Protruding between staminate flowers, firmly fixed to the main axil.

Roots: White to light purple with fine hairy laterals.

General observations: Champion is a compact and full plant. The leaves are, in relation to the flowers, very small. The leaves are coriaceous, decorative and extremely durable. Champion has unique, bright, long-lived, two-colored flowers that change color as it ages. Compared to other Anthurium cultivars of this type there are numerous axillary shoots.

I claim:

1. A new and distinct cultivar of Anthurium plant named Champion, as illustrated and described.

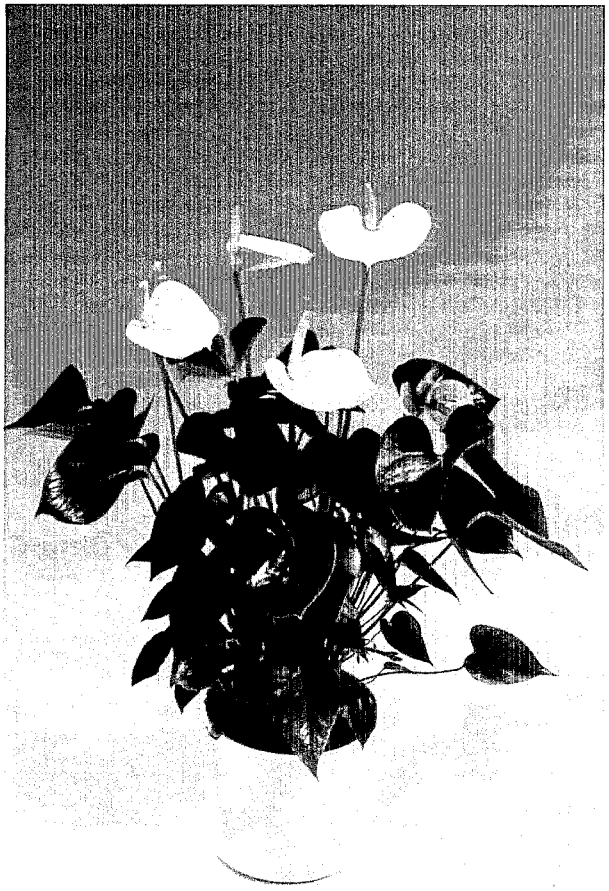

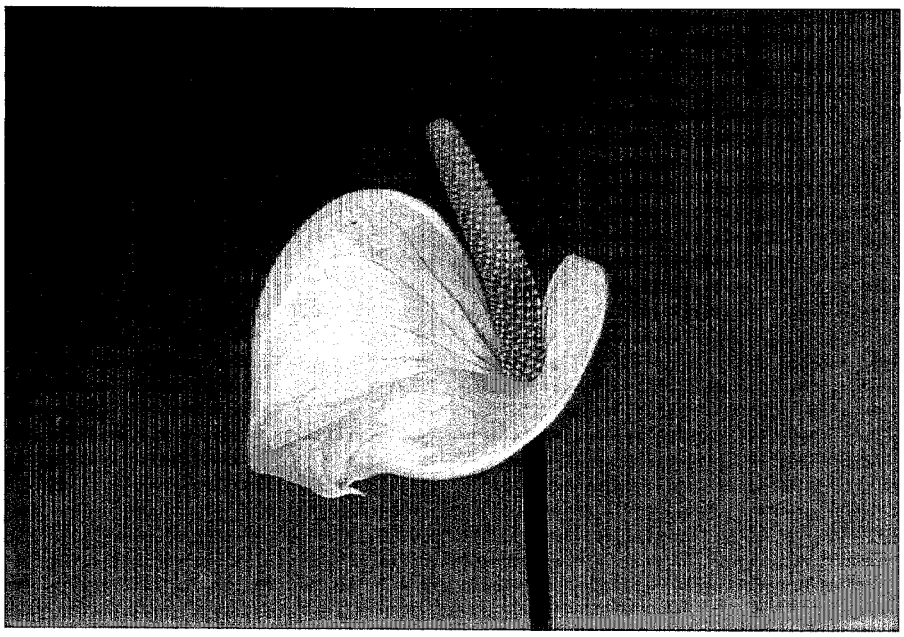

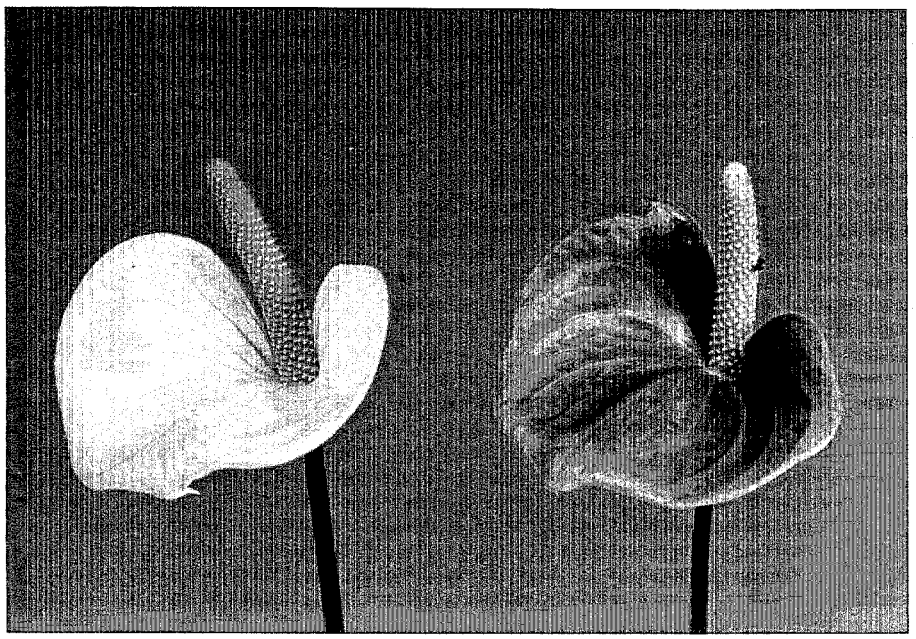

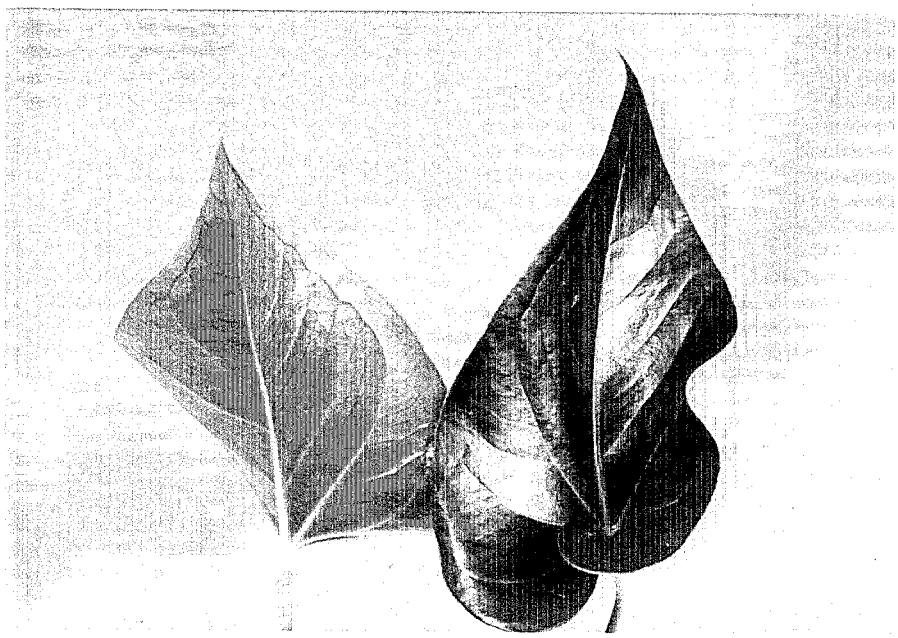

* * * * *